United States Patent
Bader

(10) Patent No.: US 7,354,764 B2
(45) Date of Patent: Apr. 8, 2008

(54) METHOD AND DEVICE FOR CULTURING CELLS

(75) Inventor: Augustinus Bader, Parthenstein-Klinga (DE)

(73) Assignee: Bionethos Holding, Parthenstein-Klinga (DE)

( * ) Notice: Subject to any disclaimer, the term of this patent is extended or adjusted under 35 U.S.C. 154(b) by 0 days.

(21) Appl. No.: 10/523,454

(22) PCT Filed: Jul. 28, 2003

(86) PCT No.: PCT/EP03/08325

§ 371 (c)(1),
(2), (4) Date: Mar. 22, 2005

(87) PCT Pub. No.: WO2004/012782

PCT Pub. Date: Feb. 12, 2004

(65) Prior Publication Data

US 2005/0221485 A1 Oct. 6, 2005

(30) Foreign Application Priority Data

Jul. 30, 2002 (DE) .............................. 102 34 742

(51) Int. Cl.
*C12N 5/00* (2006.01)
(52) U.S. Cl. .................. 435/395; 435/402; 435/325
(58) Field of Classification Search .................. None
See application file for complete search history.

(56) References Cited

U.S. PATENT DOCUMENTS 5,843,766 A * 12/1998 Applegate et al. ....... 435/284.1
5,858,747 A * 1/1999 Schinstine et al. ......... 435/182
6,468,792 B1 10/2002 Bader
2003/0186217 A1 10/2003 Bader

FOREIGN PATENT DOCUMENTS

| | | |
|---|---|---|
| DE | 197 19 751 A1 | 11/1998 |
| DE | 199 35 643 A1 | 2/2001 |
| DE | 101 04 008 A1 | 8/2002 |
| WO | WO 01/09282 * | 2/2001 |
| WO | WO-02/24861 A2 | 3/2002 |

OTHER PUBLICATIONS

U.S. Appl. No. 10/048,440, National Stage application of PCT/EP00/06153; relied upon as translation of WO 01/09282, 2001.*
Current Protocols in Cell Biology, "Preparation of Gelled Substrates" contributed by Hynda Kleinman, 1998, John Wiley & Sons, Inc, Unit 10.3 (10.3.1-10.3.9).*

* cited by examiner

*Primary Examiner*—Leon B. Lankford
*Assistant Examiner*—Allison M. Ford
(74) *Attorney, Agent, or Firm*—Davis Bujold & Daniels, P.L.L.C.

(57) ABSTRACT

In a method for culturing cells (2), according to which cells (2) are introduced into a cell culture chamber in order to form a cellular layer, the chamber being configured inside a carrier structure (1). The shape and size of the carrier structure (1) correspond to the shape that is to be formed by the cells (2), such as an implant or a prosthesis. Nutrients and oxygen are fed to the carrier structure (1). The exterior of the carrier structure (1) is provided with a boundary membrane (4) that is impermeable to cells.

22 Claims, 3 Drawing Sheets

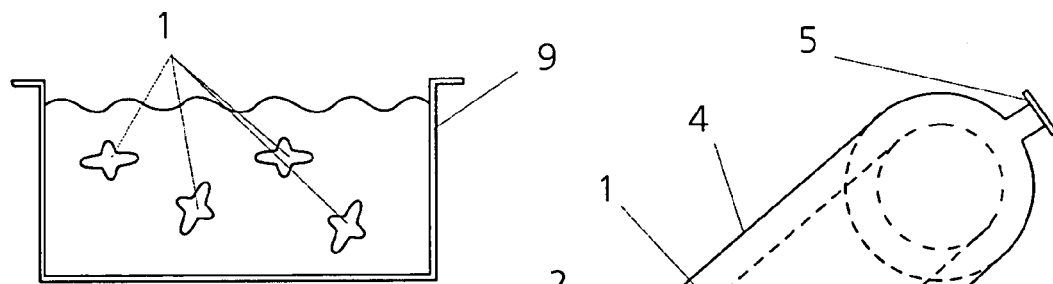
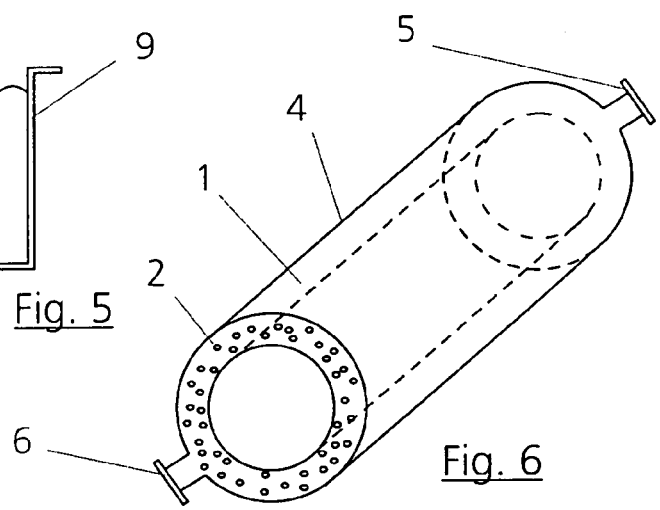
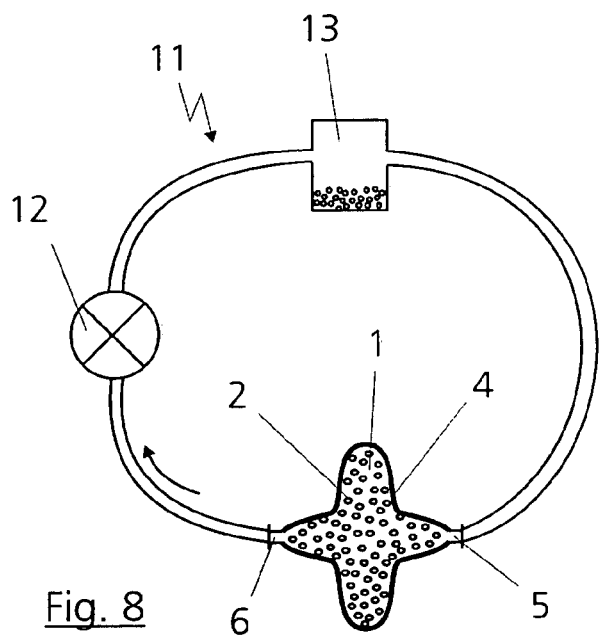
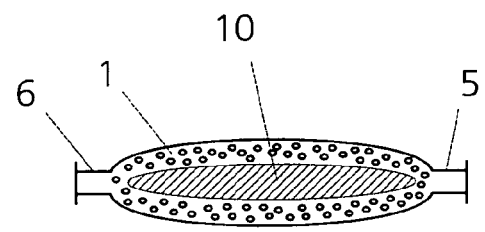
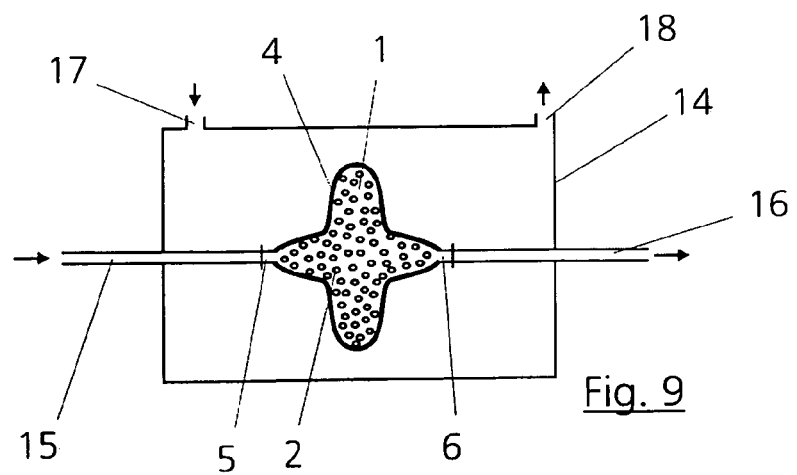

METHOD AND DEVICE FOR CULTURING CELLS

The invention relates to a method for culturing cells, the cells being introduced into a cell culture chamber to form a cell layer. The invention also relates to an apparatus for culturing cells and a support structure therefor.

DE 199 35 643 A1 describes a method and an apparatus for culturing cells, cells being cultured on a support in a malleable cell culture chamber between films. The support is introduced in this case together with the films into a container as bioreactor, nutrients and oxygen being supplied from outside.

A similar method and an apparatus therefor is also disclosed by DE 197 19 751 A1. The cell growth in this case is more or less "uncontrolled". The size of the apparatus is predetermined by the container in which the cell layer to be formed, or an implant, is located.

The object underlying the present invention is to provide a method and an apparatus for culturing cells, which method can be used in a very versatile manner, in particular shapes formed from the cells, such as implants or prostheses, being able to be produced in a very complex shape and in exactly definable size.

According to the invention this is achieved in a method for culturing cells, the cells, for formation of a cell layer, being introduced into a cell culture chamber in such a manner that the cell culture chamber is formed in the interior of a support structure, the support structure corresponding in its shape and size at least approximately to the shape to be formed by the cells, such as an implant or a prosthesis, nutrients and/or oxygen being supplied to the support structure, and the support structure being furnished externally with a boundary layer which is impermeable to cells.

According to the invention the support structure is then the actual bioreactor itself, whereas previous bioreactors have only possessed defined simple geometric shapes, for example round or square, flat or bottle-shaped. The external boundary layer which is impermeable to the cells gives an exactly defined cell culture chamber size and shape, the size and shape themselves being predetermined by the support structure. This means that the support structure can be formed exactly in the shape as the shape to be formed, for example the implant or the prosthesis, is to appear later in the final state. The implant to be manufactured is preset in practice. Thus, for example, using a computer tomogram, by which, for example, a defect vertebra is recognized, this can be reproduced exactly as support structure. The cells are then correspondingly introduced into the support structure which has been appropriately furnished with the boundary layer. Preferably, for this, the support structure is formed from a microporous, or else coarsely porous material. In this cases, the support structure can be constructed as a removable or else a convertible place holder material, so that the cell layer can form in accordance with the desired implant.

The boundary layer can be formed from a plastic which is impermeable to cells and, for this, can be applied, for example by injection or by a dipping bath.

Materials which have proved to be suitable for this are, for example, liquid or viscous polymers, silicones, polyurethanes, proteins, alginates or resins.

Alternatively, the boundary layer can also be formed from a biological material, for example a hydrogel or alginate. When an alginate is used, this can be polymerized in a calcium chloride solution and thus made impermeable to cells. For the subsequent removal and after completion of the implant, the polymerized alginate can be introduced into a low-calcium solution, whereby it redissolves.

If a self-dissolving boundary layer is not used, this can also be removed mechanically after the completion of the cell culture method.

Advantageous developments and embodiments of the invention result from the remaining subclaims and from the exemplary embodiments described hereinafter with reference to the drawing.

In the drawings:

FIG. 5 shows a container having a nutrient solution together with a plurality of implants;

FIG. 6 shows an implant in tubular bone shape;

FIG. 7 shows a partial implant for a heart valve;

FIG. 8 shows the implant shown in FIG. 3 in a nutrient circuit;

FIG. 9 shows the implant shown in FIG. 3 in a pressurizable container;

Figure 1:
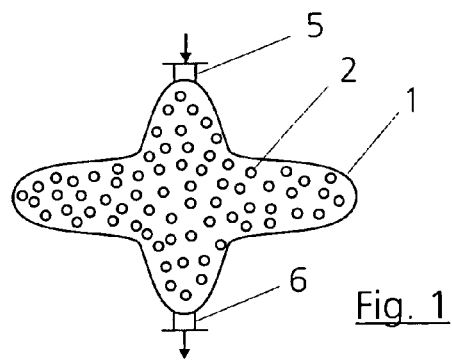
FIG. 1 shows a vertebra as an implant to be formed, in highly simplified representation.

FIG. 1 diagrammatically shows the shape of a vertebra, on the basis of which the invention will be described in more detail below. Obviously, the vertebra is only to be considered as one possible example of a prosthesis or implant. The starting point for the vertebra is a support structure 1 which consists of a porous material, for example microporous or else coarsely porous. As material for the support structure 1, use can be made of a stable, biodegradable or else remodelable material. Thus, for example, bone substitute material or else calcium phosphate can be used. Plastics and hybrid structures, in which an industrial material is combined with a biological material, are possible. What is essential is only that materials are used which are inert to cells 2 to be introduced or which do not damage the cells which are introduced or permit themselves to be modified by the cells 2.

Figure 2:
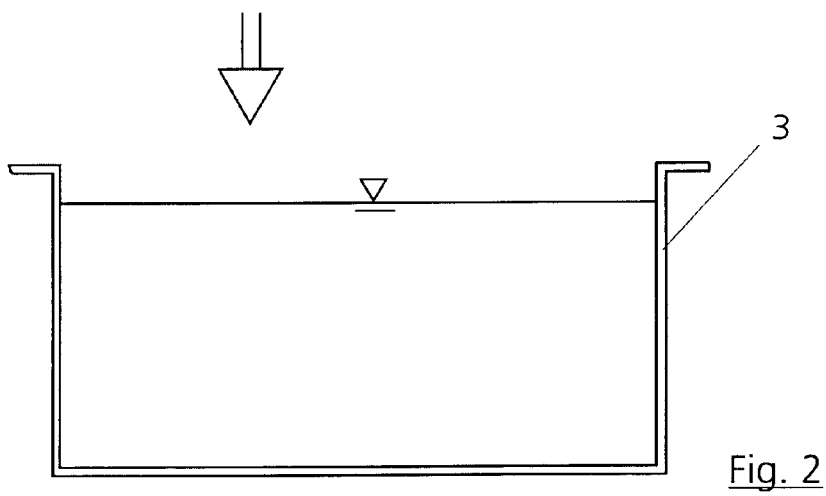
FIG. 2 shows a dipping bath for the vertebra according to FIG. 1.
Figure 3:
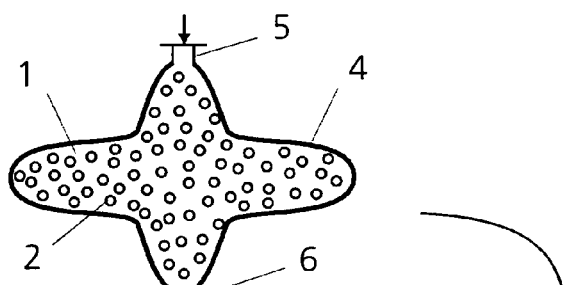
FIG. 3 shows the vertebra according to FIG. 1 having a boundary layer.

For a defined cell culture chamber to be provided in the interior of the support structure 1 for the cells 2, and for the size and shape of the implant to be formed to be maintained, it is necessary to ensure that the outer wall of the support structure 1 is impermeable to cells. For this, the support structure 1, before the introduction of the cells 2, can be immersed, for example, in a dipping bath 3 (see FIG. 2). The dipping bath 3 can be, for example, a liquid or viscous polymer which forms a boundary layer 4 (see FIG. 3) for the otherwise porous support structure 1. As polymers for forming a boundary layer, use can be made of, for example, resins.

Instead of a polymer to encapsulate the support structure 1 by forming a boundary layer 4, alternatively use can be made of an alginate material which is polymerized in a calcium chloride solution in the dipping bath 3. Such a boundary layer 4 is biologically compatible.

The boundary layer 4 can be formed so as to be sealed absolutely tightly.

However, it is advantageous if it is formed to be at least gas-permeable. In this case, oxygen can be introduced through the boundary layer 4. Likewise, it is also possible to form a boundary layer 4 which is microporous in such a manner that nutrients also diffuse through the boundary layer 4 into the interior of the support structure 1, or a mass transfer with the support structure, that is to say the later implant, takes place.

For the supply of cells 2, nutrient medium and if appropriate an oxygen carrier medium, for example fluoride solutions, blood or blood substitutes, the support structure 1 can be furnished with a feed connection 5. If, in the feed connection 5, nutrients are to be introduced into the support structure 1, the support structure 1 can also be furnished with an outlet connection 6, which provides through flow. The feed connection 5 and the outlet connection 6 can be introduced onto the support structure 1 upstream of the dipping bath 3 or else downstream of the dipping bath 3, in which case, obviously, it is necessary to ensure that no impermeable boundary layer 4 is provided in the feed region and in the outlet region.

The support structure 1 can be constructed as a removable or else modifiable place holder material for the cells 2 to be introduced. For instance, a material can be used, for example for the support structure 1, which material is dissolved on addition of cells inherent to the body, for example by enzymes. In this manner, a matrix inherent to the body is formed which is patient specific.

As boundary layer 4, use can also be made of a gel which forms a closed membrane as a boundary layer.

Figure 4:
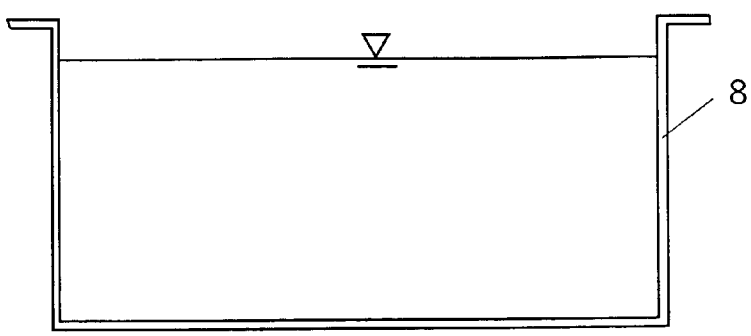
FIG. 4 shows a solution bath for the boundary layer.

After completion of the cell-formation process, or of the implant formed from the cells 2, the boundary layer 4 must be removed again. If it is of biological material, it can correspondingly be degraded again biologically, as is the case, for example, with gels or alginates. For this, the support structure 1 having the boundary layer 4 can, in accordance with FIG. 4, again be immersed in a bath 7 which degrades the boundary layer 4. When alginates are used, a solution can be used for this which removes calcium so that the boundary layer 4 dissolves correspondingly. The boundary layer 4 can also be constructed in such a manner that it dissolves itself by an enzymatic or a hydrolytic process. The boundary layer 4 can also be vascularized or prevascularized (for example by endoter- or stem cells).

When use is made of plastics or silicone which cannot be dissolved in a simple manner, the boundary layer 4 can if appropriate also be removed mechanically. To facilitate such removal, it is possible to dispose, between the support structure 1 and the boundary layer 4, an intermediate layer which does not bind to the material of the support structure 1. By means of this intermediate layer, the boundary layer 4 may then be detached more readily. For this, use can be made of, for example, a lipid layer, a protein layer and/or albumin layer, or other soluble or detachable layers (biodegradable or erodable layers).

Instead of a supply of cells 2 via the feed connection 5, if appropriate, the support structure 1 can alternatively be immersed, for example, in an aqueous or pasty solution in which cells 2 together with nutrient solution are situated. In this case, the support structure 1 is correspondingly filled by absorption with cells 2 and nutrient solution. Then, the encapsulation by a boundary layer 4 in the dipping bath 3 is performed.

Instead of a dipping bath 3, obviously a boundary layer 4 can also be sprayed on or painted on as barrier for the cells 2.

FIG. 5 shows an embodiment in which a plurality of support structures 1 furnished with boundary layers 4 are introduced into a nutrient medium bath 9 so that the growth process starts. If appropriate, here also an oxygen feed into the nutrient medium bath 9 in addition can be provided.

FIG. 6 shows, as use example, a support structure 1 in the form of a tubular bone which is likewise provided with the boundary layer 4 internally and externally, and likewise can have a feed connection 5 and an outlet connection 6. Then, into the interior of the support structure 1, it is possible to introduce stem cells which originate from the bone marrow, which can be obtained, for example, by biopsy as the cells. The stem cells then form, from the foreign support structure material, increasingly, in a time-dependent manner, their own bone material. Obviously, the material of the support structure 1 must then be correspondingly soluble, for example formed from calcium phosphate.

FIG. 7 shows as a detail a heart valve having a stainless steel part, for example titanium part 10, around which is disposed externally the support structure 1, likewise a structure 1, likewise a feed connection 5 and an outlet connection 6 being able to be provided. In this case, together with the titanium part 10, a support structure 1 is provided which reproduces the shape of a heart valve. Instead of the use of titanium 10, a polyurethane prosthesis can also be used as a heart valve.

FIG. 8 shows in principle the arrangement of a support structure 1 together with cells 2 and a boundary layer 4 in a circuit 11 having a pump 12 and a media reservoir 13. In the media reservoir 13, cells and/or nutrient solution can be disposed. An oxygen carrier can also be incorporated into the circuit 11.

FIG. 9 shows the arrangement of a support structure 1 in a container 14 into which opens out a feed line 15 for nutrients and/or oxygen, which feed line is connected to the feed connection 5. An outlet line 16 leads out of the container 14 and is connected to the outlet connection 6.

In addition, the container 14 is furnished with a connection 17 for introducing pressure medium and, if appropriate, also to outlet 18 for removal thereof. As pressure medium, use can be made of a gas or a liquid medium.

This is because it has been found that the formation of a cell layer and the cell growth are markedly improved if the cells 2 are exposed to a pressure stress. In this manner, still better in-vivo conditions are created.

As a result of the exposure of the support structure 1 to pressure via the pressurized container 14, exposure to pressure over a large surface area is achieved which simulates in-vivo conditions very well. In this case the pressure stresses can also be applied in alternation.

Figure 10:
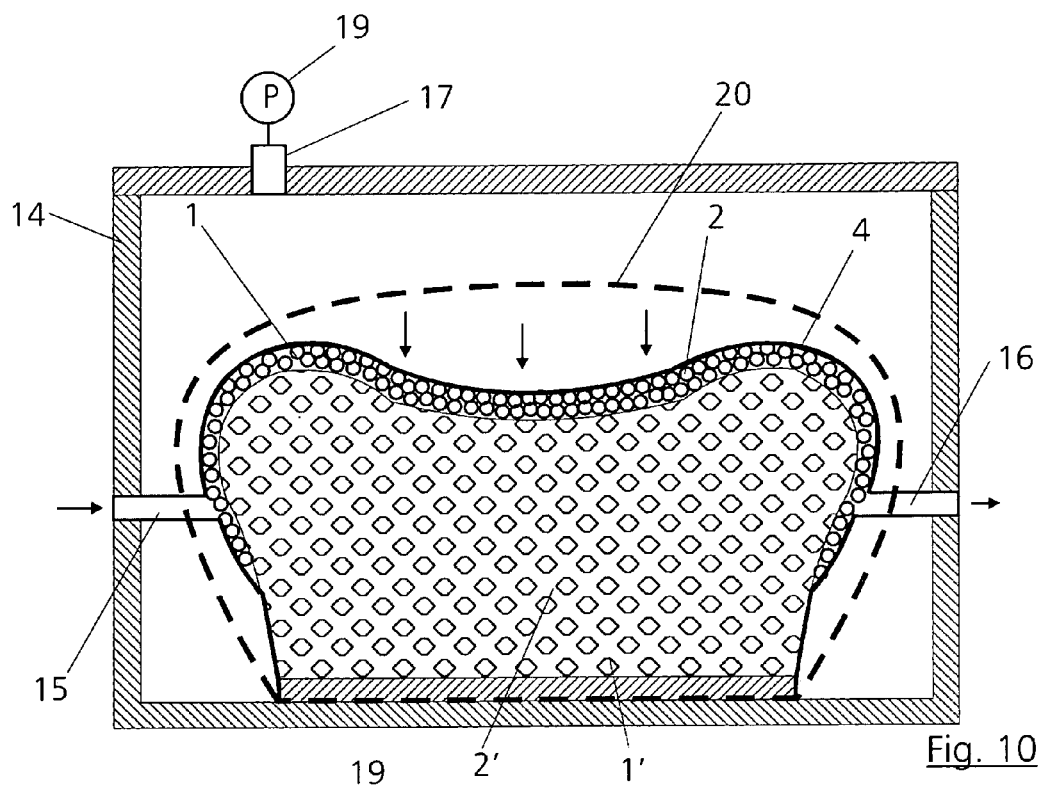
FIG. 10 shows a support structure in the form of a knee joint in a container.

FIG. 10 shows for this a possible embodiment for joint cartilages which are cultured on a support structure 1 which is to represent a knee joint.

For the knee joint, which likewise can be a support structure 1', for example of tricalcium phosphate, cells 2' can likewise be introduced in a manner not shown in more detail. If appropriate, for delimitation between the support structure 1' and the support structure 1, in which cartilage cells 2 are cultured, a boundary layer can be introduced, so as to introduce a clear separation between the cells 2 and 2'.

Via the feed connection 17, the interior of the container 14 is exposed to pressure by a pump 19. By means of the pump 19, changing pressure can be introduced into the interior of the container 14. As shown, in this case an outlet connection 18 is not necessarily present.

As indicated dashed in FIG. 10, around the two support structures 1 and 1', in addition a protective film 20 can be disposed. The protective film 20 can be provided for transport of the unit of the two support structures 1 and 1' and can seal this unit correspondingly in a sterile manner. The formation as elastically extensible film 20 ensures that the pressure stress applied by the pump 19 is transmitted to the support structures 1 and 1'.

Instead of tricalcium phosphate for the support structures 1 and 1', in the bone substitute field, collagens can also be used, in which case, for example, a meniscus can also be cultured. Likewise, connective tissue structures, polymers such as polylactides or other chemical structures can be used. What is essential is only that from these materials, shapes can be constructed which correspond to the desired implant.

In addition, the container 14 may, in case of need, also be provided with electrical connections by means of which, via connection lines which are not shown, electrical impulses can be applied to the cells 2 and 2', by which, likewise, still better in-vivo simulations can be achieved.

Figure 11:
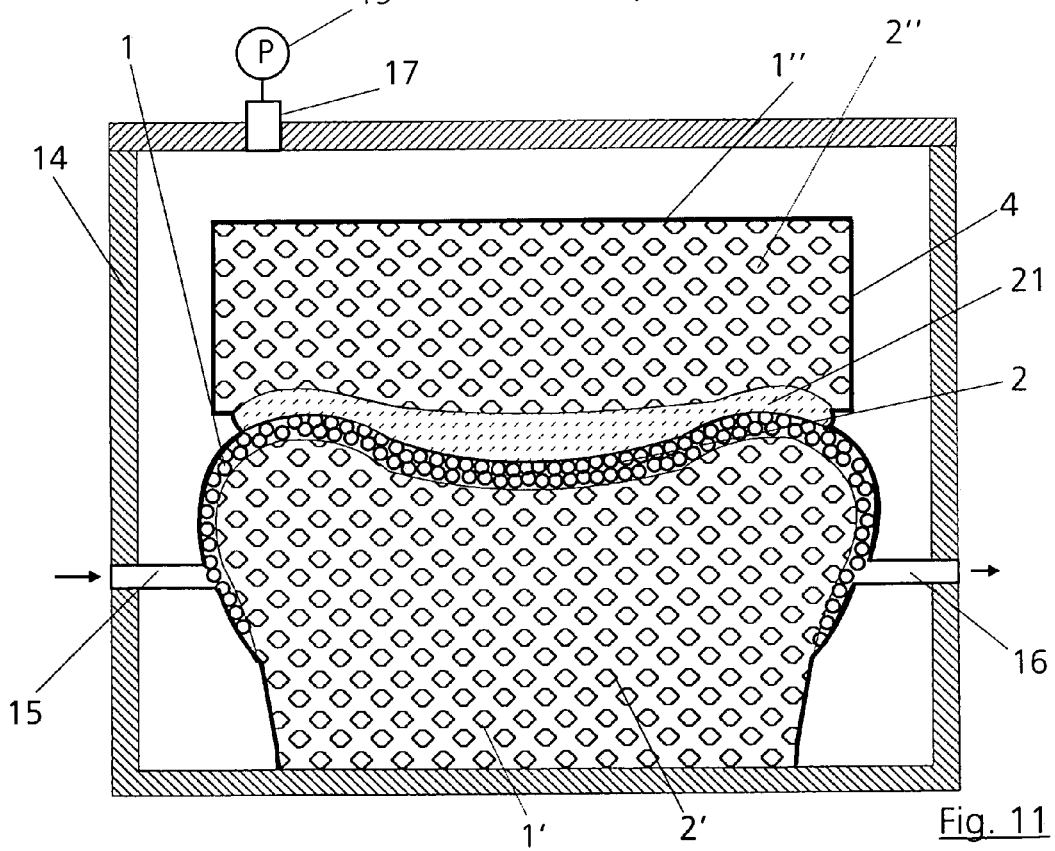
FIG. 11 shows the support structure according to FIG. 10 having an additional meniscus structure.

The embodiment shown in FIG. 11 essentially corresponds to the form described in FIG. 10, for which reason the same reference symbols have also been retained for the same parts.

The only difference is that, in addition, a meniscus structure 21 has been applied over which, in turn, a support structure 1" is situated.

For simplicity, in this case, a boundary layer 4 which is impermeable to cells 2 has been provided over the entire unit.

The boundary layer 4 can also be formed by the cells themselves which are used to culture a membrane. On the support structure 1 then, for example, connective tissue is formed as encapsulation. This can proceed, for example, by overgrowth processes with cells, for example chondrocytes, fibroblasts or osteoblasts. These cells are then in practice packaging cells and a boundary layer for the cells 2 to be cultured.

The invention claimed is:

1. A method of forming an implantable tissue construct for replacement of a human body part, the method comprising the steps of:
   a) forming an inert material into a porous support structure having a predetermined shape and size corresponding to the shape and size of a human body part to be replaced, and which substantially maintains the shape and size of the human body part to be replaced;
   b) encapsulating the entire porous support structure with a boundary layer of cell-impermeable material, which substantially conforms to the predetermined shape and size of the porous support structure;
   c) introducing living cells into the porous support structure;
   d) promoting cell growth by introducing nutrients and oxygen to the living cells in said porous support structure;
   e) after completion of cell growth, removing the boundary layer; and
   f) eliminating the porous support structure; thereby producing an implantable tissue construct having a shape and size corresponding to the human body part to be replaced.

2. The method according to claim 1, wherein the step f) of eliminating the porous support structure (1) comprises either mechanically removing or biologically degrading the support structure.

3. The method according to claim 1, wherein the inert material used to form the porous support structure is phosphate.

4. The method according to claim 1, wherein the cell-impermeable boundary layer (4) is a biological material or a synthetic material.

5. The method according to claim 4, wherein the cell-impermeable boundary layer (4) is a hydrogel material.

6. The method according to claim 1, wherein the cell-impermeable boundary layer material (4) is gas permeable.

7. The method according to claim 1, wherein the step b) of encapsulating the porous support structure with the cell-impermeable boundary layer material (4) comprises one of spraying the porous support structure with the cell-impermeable boundary layer material or dipping the porous support structure in a bath (3) of the cell-impermeable boundary layer material.

8. The method according to claim 1, further comprising, between steps a) and b), a step a') forming an intermediate layer, between the porous support structure (1) and the boundary layer (4), from a material which remains unbound to the support structure (1) so that the intermediate layer facilitates removal of the boundary layer from the porous support structure.

9. The method according to claim 8, wherein the intermediate layer is a lipid layer.

10. A method of forming an implantable tissue construct for replacement for a human body part, the method comprising the steps of:
    a) forming an inert material into a porous support structure having a shape and size corresponding to the shape and size of a human body part to be replaced;
    b) enclosing the entire porous support structure within a contiguous boundary layer of cell-impermeable material;
    c) providing the porous support structure with at least one inlet;
    d) introducing living cells into the porous structure;
    e) promoting cell growth within the porous support structure, by introducing nutrients and oxygen to the living cells, so that the cells conform to the size and shape of the porous support structure; and
    f) removing the boundary layer; thereby producing an implantable tissue construct having a size and shape corresponding to the shape and size of the human body part to be replaced.

11. The method according to claim 10, further comprising a step g) eliminating the porous support structure (1) by either mechanically removing, or biologically degrading the support structure.

12. The method according to claim 10, wherein the inert material used to form the porous support structure is phosphate.

13. The method according to claim 10, wherein the cell-impermeable boundary layer (4) is a biological material or a synthetic material.

14. The method according to claim 13, wherein the cell-impermeable boundary layer (4) is a hydrogel material.

15. The method according to claim 10, wherein the cell-impermeable boundary layer material (4) is gas permeable.

16. The method according to claim 10, wherein the step b) of enclosing the porous support structure with the cell-impermeable boundary layer material (4) comprises one of spraying the porous support structure with the cell-impermeable boundary layer material or dipping the porous support structure in a bath (3) of the cell-impermeable boundary layer material.

17. The method according to claim 10, further comprising, between steps a) and b), a step a') forming an intermediate layer, between the porous support structure (1) and the boundary layer (4), from a material which remains unbound to the support structure (1) so that the intermediate layer facilitates removal of the boundary layer from the porous support structure.

18. The method according to claim 17, wherein the intermediate layer is a lipid layer.

19. The method according to claim 10, further comprising a step g) eliminating the porous support structure from the implantable tissue construct.

20. The method according to claim 10, further comprising the step of removing the boundary layer (4) from the implantable tissue construct by one of:
   mechanically detaching the boundary layer from the porous support structure, and
   solubilizing the boundary layer.

21. A method of forming an implantable tissue construct for replacement of a human body part, the method comprising the steps of:
   a) forming an inert material into a porous support structure having a predetermined shape and size corresponding to the shape and size of a human body part to be replaced, and which substantially maintains the shape and size of the human body part to be replaced;
   b) encapsulating the entire porous support structure with a boundary layer of cell-impermeable material, which substantially conforms to the predetermined shape and size of the porous support structure;
   c) introducing living cells into the porous support structure;
   d) promoting cell growth by introducing nutrients and oxygen to the living cells in said porous support structure;
   e) after completion of cell growth, removing the boundary layer from the porous support material by mechanically detaching the boundary layer; and
   f) solubilizing the porous support structure; thereby producing an implantable tissue construct having a shape and size corresponding to the human body part to be replaced.

22. A method of forming a plurality of implantable tissue constructs for replacement of human body parts, the method comprising the steps of:
   a) forming inert material into a plurality of porous support structures, each support structure having a predetermined shape and size corresponding to the shape and size of a human body part to be replaced, and which substantially maintain the shape and size of the human body part to be replaced;
   b) completely encapsulating each of the porous support structures with a boundary layer of cell-impermeable material, which substantially conforms to the predetermined shape and size of each of the porous support structures;
   c) introducing living cells into each of the porous support structures;
   d) promoting cell growth in each of the porous support structures by introducing nutrients and oxygen to the living cells in each of said porous support structures; and
   e) introducing a plurality of the porous support structures (1) into a nutrient solution to facilitate cell growth; and
   f) after completion of cell growth, removing the boundary layer from each of the porous support structures; thereby producing a plurality of implantable tissue constructs each having a shape and size of the human body part to be replaced.

* * * * *